United States Patent [19]

Gadient

[11] Patent Number: 5,534,503
[45] Date of Patent: Jul. 9, 1996

[54] 2'-O, $N^6$-DISUBSTITUTED AND 2'-O, $N^6$, 2-TRISUBSTITUTED ADENOSINES AND THEIR MEDICINAL USES

[75] Inventor: Fulvio Gadient, Birsfelden, Switzerland

[73] Assignee: Sandoz Ltd., Basel, Switzerland

[21] Appl. No.: 330,043

[22] Filed: Oct. 27, 1994

Related U.S. Application Data

[63] Continuation of Ser. No. 106,004, Aug. 13, 1993, abandoned, which is a continuation of Ser. No. 449,020, Dec. 11, 1989, abandoned.

[30] Foreign Application Priority Data

Dec. 13, 1988 [DE] Germany ............. 38 41 881.9

[51] Int. Cl.$^6$ ............. A61K 31/70; C07H 19/167
[52] U.S. Cl. ............. 514/46; 536/27.62; 536/27.63
[58] Field of Search ............. 536/27.63, 27.62; 514/46

[56] References Cited

U.S. PATENT DOCUMENTS

| | | | |
|---|---|---|---|
| 3,471,472 | 10/1969 | Thiel et al. | 536/27.62 |
| 4,843,066 | 6/1989 | Yamada et al. | 514/45 |
| 4,962,194 | 10/1990 | Bridges | 536/27.11 |
| 4,985,409 | 1/1991 | Yamada et al. | 514/46 |
| 5,032,583 | 7/1991 | Evans | 514/46 |

OTHER PUBLICATIONS

Robert F. Bruns, et al. Molecular Pharmacology 29:331–346 (1986).

Kikugawa, et al., J. Med. Chem., vol. 16, No. 4 (1973), pp. 358–364.

Goodman, "Chemical Syntheses and Transformations of Nucleosides," Ch. 2 in *Basic Principles in Nucleic Acid Chemistry*, vol. 1, P.O.P. Ts'O (ed.), Academic Press, New York, New York, 1974, see pp. 144–145.

Robins et al., "Sugar–Modified $N^6$–(3–Methyl–2–butenyl)adenosine Derivatives, $N^6$–Benzyl Analogs, and Cytokinin–Related Nucleosides Containing Sulfur or Formycin," *Biochemistry*, 12(12), 2179–2187 (1973).

Primary Examiner—Douglas W. Robinson
Assistant Examiner—L. Eric Crane
Attorney, Agent, or Firm—Robert S. Honor; Melvyn M. Kassenoff; Thomas O. McGovern

[57] ABSTRACT

Adenosines derivatives of the formula

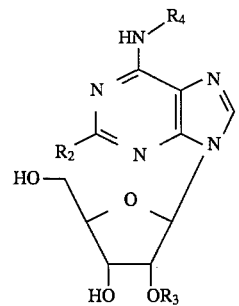

wherein $R_1$ is allyl, methallyl, straight or branched chain $(C_{3-7})$alkynyl, $(C_{3-8})$cycloalkyl, or phenyl mono- or independently of one another di-substituted by halogen having an atomic number of from 9 to 35, $(C_{1-4})$alkyl, $(C_{1-4})$alkoxy, or $CF_3$; $R_2$ is hydrogen or $C_{(1-4)}$alkyl, and $R_3$ is $(C_{1-4})$alkyl, are useful for protecting vascular endothelium, for lowering blood lipid levels, and for treating raised blood pressure.

16 Claims, No Drawings

2'-O, N⁶-DISUBSTITUTED AND 2'-O, N⁶, 2-TRISUBSTITUTED ADENOSINES AND THEIR MEDICINAL USES

This is a continuation of application Ser. No. 08/106,004, now abandoned, filed Aug. 13, 1993, which in turn is a continuation of application Ser. No. 07/449,020, filed Dec. 11, 1989, now abandoned.

The invention relates to new 6-alkenyl-, alkinyl-, cycloalkyl-, aryl- or aralkyl-2'-O-alkyladenosine derivatives, a process for their production and their use, among other things, for the treatment of raised blood pressure.

The invention especially relates to 6-alkenyl-, alkinyl-, cycloalkyl-, aryl- or aralkyl-2'-O-alkyladenosine derivatives of formula I,

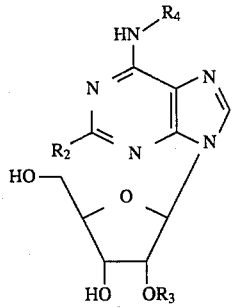

wherein $R_1$ singifies allyl, methallyl, a straight-chain or branched $(C_{3-7})$alkinyl, $(C_{3-8})$cycloalkyl, phenyl being independently of one another mono- or disubstituted by halogen with an atomic number of 9 to 35, $(C_{1-4})$alkyl, $(C_{1-4})$alkoxy or $CF_3$, or phenyl $(C_{2-4})$alkyl whereby the phenyl ring is optionally independently of one another mono- or disubstituted by halogen with an atomic number of 9 to 35, $(C_{1-4})$alkyl, $(C_{1-4})$alkoxy or $CF_3$, $R_2$ is hydrogen, $(C_{1-4})$alkyl, $(C_{3-5})$cycloalkyl or halogen with an atomic number of 9 to 35 and $R_3$ is $(C_{1-4})$alkyl.

Of the compounds of formula I, the preferred compounds possess the formula

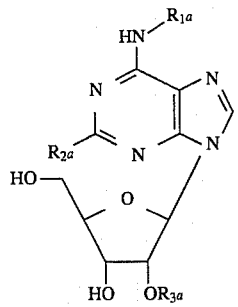

wherein $R_1^a$ signifies allyl, prop-2-ynyl, cyclopropyl, cyclopentyl, cyclohexyl, cycloheptyl, p-methoxyphenyl, p-chlorophenyl, p-fluorophenyl, (R)-phenyl-$CH_2$—$CH(CH_3)$—

$R_2^a$ signifies hydrogen, methyl, cyclopentyl or bromine and $R_3^a$ signifies methyl or ethyl.

In formula I, halogen with an atomic number of 9 to 35 is fluorine, chlorine or bromine, $(C_{1-4})$alkyl is methyl, ethyl, n-propyl, i-propyl, n-butyl, i-butyl, tert.-butyl, and $(C_{1-4})$alkoxy is methoxy, ethoxy, n-propoxy, i-propoxy, n-butoxy, i-butoxy, tert.-butoxy. When $R_1$ is phenyl $(C_{2-4})$alkyl, the alkylene group may be straight-chain or branched and signifies for example ethylene or isopropylene. Alkinyl which may be straight-chain or branched signifies especially prop-1-ynyl, prop-2-ynyl and but-2-ynyl. $(C_{3-8})$cycloalkyl stands for cyclopropyl, cyclobutyl, cyclopentyl, cyclohexyl, cycloheptyl or cyclooctyl.

The process for the preparation of compounds of formula I is characterised in that compounds of formula

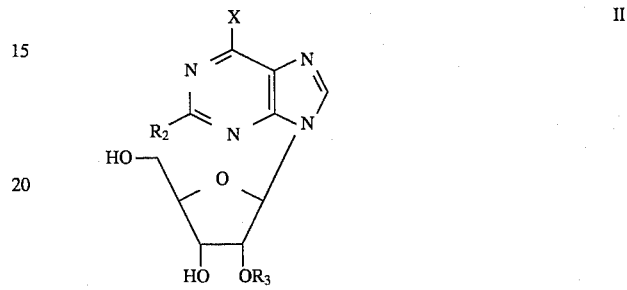

wherein $R_2$ and $R_3$ possess the significances given above and

X is halogen are reacted with a compound of formula $$R_1-NH_2 \qquad III$$

wherein $R_1$ possess the significance given above.

The above process is conveniently effected by heating compounds of formula II together with compounds of formula III to temperatures of 80° to 120° C, preferably to boiling temperature, optionally in the presence of a solvent such as dioxane.

In the compounds of formula II, which are used as starting compounds in this process, X is suitably chlorine or bromine, especially chlorine. The compounds of formula II, as well as a process for the production thereof, are described in published European patent application 269 574.

The 6-alkenyl-, alkinyl-, cycloalkyl-, aryl- or aralkyl-2'-O-alkyl adenosin derivatives of formula I produced in accordance with the invention are also referred to in the following as compounds according to the invention.

In the following examples, all temperatures are in degrees celsius and are uncorrected.

EXAMPLE 1: 6-CYCLOPENTYL-2'-O-METHYLADENOSINE 1.1 g of 6-chloro-9-purinyl-2'-O-methyl-D-ribose are refluxed for 2 hours at boiling in 50 ml of cyclopentylamine. The mixture is subsequently concentrated to dryness at reduced pressure, and the residue is eluted on silica gel with a mixture of methylene chloride/ethanol 9:1. The purified product is crystallised from methylene chloride/n-hexane. The compound named in the title has a m.p. of 148°–149°.

The 6-chloro-9-purinyl-2'-O-methyl-D-ribose used as starting material may be produced as follows, e.g. analogously to the method given in published Europ. patent application 269 574:

a) 18 g of 6-chloro-9-purinyl-D-ribose are stirred for 2 hours at room temperature with 20 ml of 1,3-dichloro-1,1,3,3-tetraisopropyldisiloxane in 350 ml of pyridine. The mixture is subsequently concentrated to dryness in a waterjet vacuum (11 mm Hg) at a bath temperature of 30° to 35°, the residue is dissolved in methylene chloride and the organic phase washed with an aqueous sodium bicarbonate solution and then with water. After drying over magnesium sulphate, the product is concentrated to dryness and the residue is eluted on silica gel with a mixture of ethyl acetate/n-hexane 3:7. The 6-chloro-9-purinyl-3',5'-O-(1,1,3,3-tetraisopropyldisilox- 1,3-diyl)-D-ribose has a Rf value of 0.35.

b) 4 g of 6-chloro-9-purinyl-3',5'-O-(1,1,3,3-tetraisopropyldisilox- 1,3-diyl)-D-ribose are dissolved in 140 ml of benzene, mixed with 140 ml of methyl iodide and 6 g of silver oxide, and the mixture is refluxed for 2 hours at boiling. To complete the reaction, a further 6 g of silver oxide are added, and the mixture is refluxed at boiling for a further 2 hours. It is then cooled, filtered through Hyflo and the filtrate is concentrated at reduced pressure. The raw 6-chloro-9-purinyl-2'-O-methyl-3',5'-O-(1,1,3,3-tetraisopropyldisilox- 1,3-diyl)-D-ribose is used in the next stage without further purification.

c) 4 g of the compound produced in section b) and 9.3 g of tetrabutylammonium fluoride trihydrate are stirred for 20 minutes at room temperature in 200 ml of tetrahydrofuran. The mixture is subsequently concentrated to dryness and the residue is eluted on silica gel with a mixture of methylene chloride/ethanol 9:1. The purified 6-chloro-9-purinyl-2'-O-methyl-D-ribose has a Rf value of 2.5.

The following compounds of formula I, wherein $R_1$, $R_2$ and $R_3$ are as below, are obtained analogously to example 1, using corresponding starting compounds.

| Example | $R_1$ | $R_2$ | $R_3$ | M.p. |
| --- | --- | --- | --- | --- |
| 2 | p-methoxyphenyl | H | $CH_3$ | 190–192° |
| 3 | cyclopentyl | H | $C_2H_5$ | amorph |
| 4 | cyclopentyl | $CH_3$ | $CH_3$ | 180–181° |
| 5 | cyclopentyl | Br | $CH_3$ | 150–151° |
| 6 | cyclopropyl | H | $CH_3$ | 148–149° |
| 7 | cyclohexyl | H | $CH_3$ | 90–94° (cont.1 Mol ether) |
| 8 | cycloheptyl | H | $CH_3$ | 70–80° decomp. (cont.1 Mol ethanol) |
| 9 | p-fluorophenyl | H | $CH_3$ | 226–227° |
| 10 | p-chlorophenyl | H | $CH_3$ | 238–239° |
| 11 | (R)-phenyl-$CH_2CH(CH_3)$— | H | $CH_3$ | amorph |
| 12 | allyl | H | $CH_3$ | 119–121° |
| 13 | prop-2-ynyl | H | $CH_3$ | 156–158° |

The compounds according to the invention are notable for their interesting pharmacological properties. They may therefore be used as medicaments.

In particular, the compounds according to the invention have anti-hypertensive activity, as can be deduced from the results of the following investigations:

Measurement of the binding to adenosine A1 and A2 receptors in membranes from the rat's cortex or from the cortex or striatum of the pig's brain, using the method of R. F. BRUNS, G. H. LU and T. A. PUGSLEY, which is described in MOLEC. PHARMACOL. 29, 331–346 (1986).

Further testing of the activity of the compounds according to the invention on the isolated, perfused rat's kidneys for the following parmeters:

renin secretion, renal haemodynamics (vasodilation)

Inhibition of the release of noradrenaline from the nerve endings following electro-stimulation of the renal nerves according to the method of H. J. SCHUREK, J. P. BRECHT, H. LOHFERT and K. HIERHOLZER, described in COMMUNICATION a la REUNION de l'ASSOCIATION DES PHARMACOLOGISTES LOUVIN UCL 4th June 1977, as well as P. M. VANHOUTTE, D. BROWNING, E. COEN, T. J. VERBEUREN, L. ZONNEKEYEN and M. G. COLLINS described in HYPERTENSION 4, 251–256 (1982).

Measurement of blood pressure, heart rate, urine production and renin activity in plasma of wake, NaCl-depleted and repleted, normotensive or spontaneously hypertensive rats with catheters implanted in the abdominal aorta and in the vena cava, following i.v. administration or administration of the compounds according to the invention as an infusion or bolus according to the method of J. F. M. SMITS and J. M. BRODY described in Am. J. Physiol. 247, R1 003–R1 008 (1984).

It can be deduced from the results of the examinations that both the inhibition of renin secretion and of release of noradrenaline from nerve endings, and the direct vasodilation, take part in the anti-hypertensive activity of the compounds according to the invention. Along with the strong lowering of the blood pressure the urine production and the electrolyte excretion remain unchanged. It results from this that the compounds according to the invention can not only be used as antihypertensive agents, but also effect coronary vasodilatation. Furthermore, they protect the vascular endothelium by inhibiting both thrombocyte aggregation and activation of leucocytes. They also lower blood lipid level.

For the above indications, of the compounds according to the invention, the compound of example 2 is preferred.

For the above application as anti-hypertensive agents, the dosage to be used varies according to the substance used, the type of administration and the desired treatment. In general however, satisfactory results are obtained with a daily dosage of approximately 0.01 to approximately 10 mg per kg body weight; if necessary, administration may be effected in 2 to 4 portions or even as a sustained release form. For larger mammals, the daily dosage is in the range of approximately 1 to approximately 500 mg; suitable dosage forms for e.g. oral or non-oral administration generally contain about 0.5 to 250 mg, together with solid or liquid carrier substances.

The compounds according to the invention may be administered alone or in a suitable dosage form. The medicinal forms, e.g. a solution or a tablet, may be produced analogously to known methods.

The invention therefore also relates to medicaments which contain the compounds according to the invention as well as the production of these medicaments in known manner. The ajuvants and carriers which are usual in pharmacy may be used for their preparation.

We claim:

1. A compound of formula

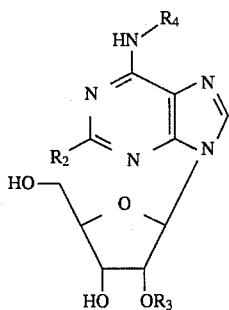

wherein
- $R_1$ signifies allyl, methallyl, a straight-chain or branched $(C_{3-7})$alkynyl, $(C_{3-8})$cycloalkyl, or phenyl being independently of one another mono- or disubstituted by halogen with an atomic number of 9 to 35, $(C_{1-4})$alkyl, $(C_{1-4})$alkoxy or $CF_3$,
- $R_2$ is hydrogen, $(C_{1-4})$alkyl, $(C_{3-5})$cycloalkyl or halogen with an atomic number of 9 to 35 and
- $R_3$ is $(C_{1-4})$alkyl.

2. A compound according to claim 1 of formula

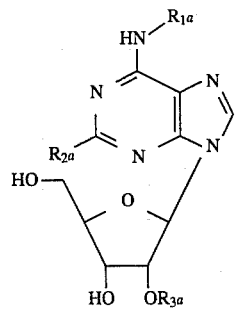

wherein
- $R_1{}^a$ signifies allyl, prop-2-ynyl, cyclopropyl, cyclopentyl, cyclohexyl, cycloheptyl, p-methoxyphenyl, p-chlorophenyl, or p-fluorophenyl,
- $R_2{}^a$ signifies hydrogen, methyl, cyclopentyl or bromine and
- $R_3{}^a$ signifies methyl or ethyl.

3. A compound according to claim 1 of the formula

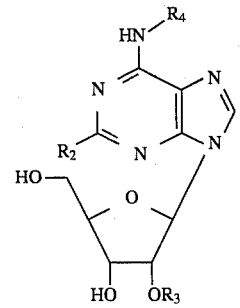

wherein $R_1$ signifies $(C_{3-8})$cycloalkyl, $R_2$ is hydrogen or $(C_{1-4})$alkyl, and $R_3$ is $(C_{1-4})$alkyl.

4. A compound according to claim 1 of the formula

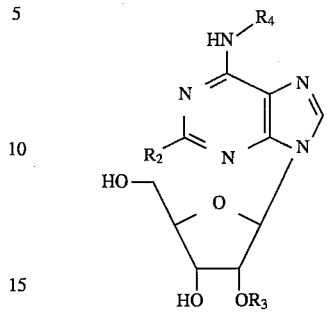

wherein $R_1$ signifies phenyl mono- or independently di-substituted by halogen having an atomic number of from 9 to 35, $(C_{1-4})$alkyl, $(C_{1-4})$alkoxy, or $CF_3$, $R_2$ is hydrogen or $(C_{1-4})$alkyl, and $R_3$ is $(C_{1-4})$alkyl.

5. The compound according to claim 3 which is $N^6$-cyclopentyl-2'-O-methyladenosine.

6. The compound according to claim 3 which is $N^6$-cyclopentyl-2'-O-ethyladenosine.

7. The compound according to claim 1 which is 2-methyl-$N^6$-cyclopentyl-2'-O-methyladenosine or 2-bromo-$N^6$-cyclopentyl-2'-O-methyladenosine.

8. The compound according to claim 3 which is $N^6$-cyclopropyl-2'-O-methyladenosine.

9. The compound according to claim 3 which is $N^6$-cyclohexyl-2'-O-methyladenosine.

10. The compound according to claim 3 which is $N^6$-cycloheptyl-2'-O-methyladenosine.

11. The compound according to claim 4 which is $N^6$-p-methoxyphenyl-2'-O-methyladenosine.

12. The compound according to claim 4 which is $N^6$-p-fluorophenyl-2'-O-methyladenosine.

13. The compound according to claim 4 which is $N^6$-p-chlorophenyl-2'-O-methyladenosine.

14. The compound according to claim 1 which is $N^6$-allyl-2'-O-methyladenosine or $N^6$-prop-2-ynyl-2'-O-methyladenosine.

15. A pharmaceutical composition comprising a therapeutically effective amount of a compound according to claim 1 and a pharmaceutically acceptable carrier therefor.

16. A method of lowering blood lipid level and treating raised blood pressure in a subject in need of said treatment, which comprises administering to the subject a therapeutically effective amount of a compound according to claim 1.

* * * * *